US 11,361,859 B2

United States Patent
Cohen et al.

(10) Patent No.: US 11,361,859 B2
(45) Date of Patent: *Jun. 14, 2022

(54) TENNIS RACKET SENSOR SYSTEM AND COACHING DEVICE

(71) Applicant: Neuro Tennis, Inc., McLean, VA (US)

(72) Inventors: Marc A. Cohen, McLean, VA (US); Alain J. Cohen, McLean, VA (US)

(73) Assignee: Neuro Tennis, Inc., McLean, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/991,338

(22) Filed: Aug. 12, 2020

(65) Prior Publication Data

US 2020/0368601 A1 Nov. 26, 2020

Related U.S. Application Data

(63) Continuation of application No. 15/928,302, filed on Mar. 22, 2018, now abandoned, which is a
(Continued)

(51) Int. Cl.
| | |
|---|---|
| *G09B 19/00* | (2006.01) |
| *G16H 20/30* | (2018.01) |
| *A63B 69/38* | (2006.01) |
| *A63B 71/06* | (2006.01) |
| *A63B 69/40* | (2006.01) |

(52) U.S. Cl.
CPC ............. *G16H 20/30* (2018.01); *A63B 69/38* (2013.01); *A63B 69/40* (2013.01); *A63B 71/0619* (2013.01); *G09B 19/0038* (2013.01); *A63B 2069/402* (2013.01); *A63B 2071/0683* (2013.01); *A63B 2208/0204* (2013.01); *A63B 2220/30* (2013.01); *A63B 2220/40* (2013.01); *A63B 2220/50* (2013.01);
(Continued)

(58) Field of Classification Search
CPC .............. G09B 19/003; G09B 19/0038; A61B 24/0003; A61B 24/0006; A61B 69/38
See application file for complete search history.

(56) References Cited

U.S. PATENT DOCUMENTS

| | | | | |
|---|---|---|---|---|
| 6,012,995 A | * | 1/2000 | Martin | .................... A63B 49/08 473/459 |
| 2007/0105664 A1 | * | 5/2007 | Scheinert | ............... A63B 49/00 473/461 |

(Continued)

*Primary Examiner* — Peter R Egloff
(74) *Attorney, Agent, or Firm* — Danielson Legal LLC

(57) ABSTRACT

Embodiments of the present invention are directed to devices, systems, and methods for measuring values obtained from one or more sensors installed on a player's tennis racket and/or worn on the player's body, and using those values to calculate various parameters, such as the physical position and motion of the tennis racket. Embodiments may translate the parameters and derive one or more occurrences corresponding to phases of a tennis point or drill and then generate real-time audible, visual, and/or haptic coaching prompts and other related commands and signals, for the purpose of improving a player's motor skills. Embodiments may also send and receive messages to/from other embodiments, thereby permitting a player to interact with other players, coaches, or devices, such as ball machines and cameras.

18 Claims, 7 Drawing Sheets

Related U.S. Application Data continuation of application No. 14/697,248, filed on Apr. 27, 2015, now Pat. No. 9,956,469.

(60) Provisional application No. 62/084,205, filed on Nov. 25, 2014.

(52) U.S. Cl.
CPC ... *A63B 2220/803* (2013.01); *A63B 2220/833* (2013.01); *A63B 2220/836* (2013.01)

(56) References Cited

U.S. PATENT DOCUMENTS

| | | | |
|---|---|---|---|
| 2013/0053190 A1* | 2/2013 | Mettler | A63B 24/0062 473/463 |
| 2013/0108995 A1* | 5/2013 | DePasqua | G09B 23/28 434/236 |

* cited by examiner

TENNIS RACKET SENSOR SYSTEM AND COACHING DEVICE

CROSS REFERENCE TO RELATED APPLICATIONS

This application claims priority to and the benefit of U.S. patent application Ser. No. 15/928,302, entitled "Tennis Racket Sensor System and Coaching Device," filed Mar. 22, 2018; which claims priority to U.S. patent application Ser. No. 14/697,248, entitled "Tennis Racket Sensor System and Coaching Device," filed Apr. 27, 2015 and issued as U.S. Pat. No. 9,956,469 on May 1, 2018; and U.S. Provisional Patent Application No. 62/084,205, entitled "Tennis Racket Sensor System," filed Nov. 25, 2014, the entire contents of each of which are hereby incorporated by reference.

FIELD OF THE INVENTION

The present invention is related to the field of athlete performance monitoring, athletic training, and coaching. More particularly, the present invention is related to the field of athlete performance monitoring, athletic training, and coaching within racket sports, e.g., the sport of tennis. Even more particularly, the present invention is related to devices, systems, and methods for sensing certain parameters relating to the motion of a racket, paddle, or club while receiving and processing event messages generated by other devices, and providing audible, visual, and/or haptic feedback, coaching prompts, and/or instructions.

BACKGROUND

It is well known in the sporting world that athletes are often intensely interested in improving their performance in a given sport. This observation is true for all levels of athletes, but it may be especially true for novice athletes who are just learning a new sport or a new skill. Some athletes learn new skills by trial and error. Other athletes receive the benefit of a trainer or instructor. Regardless of which learning process is employed, most athletes tend to go through three stages of motor skill acquisition when they are learning or improving their skills: a cognitive stage, an associative stage, and an autonomous stage.

In the cognitive stage, an athlete begins to acquire information about how to perform a new skill. The focus of the cognitive stage is the development of a mental model of movement. The athlete receives and processes new information relating to a skill and then processes that information in an attempt to cognitively understand the essential requirements and parameters of motor coordination. The cognitive stage is characterized by large gains in performance, but the performance is typically inconsistent. To improve performance consistency at this stage, techniques such as slow-motion drills, video analysis, and augmented feedback can be highly effective. It is especially important that the athlete be provided with the necessary information, guidance, and time to establish sound fundamentals of movement through cognitive processes.

In the associative stage, the learning process becomes less cognitive and more physical, as an athlete attempts to apply what he/she has learned. Here, the athlete attempts to translate cognitive knowledge into procedural knowledge. In other words, the athlete tries to transform his/her understanding about what to do into the motor knowledge of how to do it. Accordingly, there is less emphasis on processing new information at the associative stage. Instead, the athlete uses conscious processing, combined with performance feedback, to obtain better motor control. The athlete may also work at making small adjustments to various movements and stringing together short sequences of smaller movements.

In the final autonomous stage of motor acquisition, typically after years of training, physical performance can become largely automatic. Cognitive processing demands are greatly reduced, and athletes can be capable of attending to and processing other information, such as the position of opponents, game strategy, and a particular form or style of movement. This is the stage where athletes can respond almost reflexively, where they can "grip it and rip it," where they look and automatically react, and where they can enter a "zone" to achieve a state of flow.

Both good outcomes and bad outcomes are associated with the autonomous stage. Good outcomes are based on the fact that motor performance at this level requires much less cognitive demand, which thereby frees an athlete to engage in secondary tasks. On the other hand, when cognitive demand is lower, there can be more room for irrelevant and distracting thoughts. Another bad outcome during automatic motor performance is that an athlete may perpetuate incorrect movements. Just because a motor movement can be performed automatically does not mean the movement is correct or worthy of being maintained. Moreover, as soon as athletes stop thinking about a movement that was learned during the cognitive and associative stages, they may revert back to old and incorrect autonomous motor movements during competition or when they are under stress or are fatigued.

Indeed, there is always room for athletic improvement. This is true for all sports and all ages. Highly successful athletes and highly effective coaches are always looking for ways to get better. Consequently, they frequently revisit both the cognitive and associative stages of motor learning. Revisiting these stages can be essential for refining and perfecting athletic movements.

In the sport of tennis, for example, it is necessary to learn not only the rudimentary movements required to hit a ball, but also to quickly recognize, react, and respond to the movements of an opposing player. (The terms "athlete" and "player," as used herein, are intended to have the same meaning.) Indeed, an ability to recognize and react to an opponent's shot can determine whether a player is able to get in position to hit a ball, able to hit a weak defensive shot, or able to hit a strong winning shot.

A quick reaction to the movements of an opposing player can depend on an ability to anticipate, and the ability to anticipate can depend on an ability to read cues from an opposing player. Recent research has shown that one of the differences between an expert and a novice tennis player is where a player is looking (i.e., directing his/her attention) when an opponent hits the ball. In addition to a player's focus of attention, proficiency in tennis also depends on a player's efficiency of movement. Players and coaches can use many drills to improve movement efficiency. Drills can also help to train player attention and focus through proper anticipation, observation, and identification of an opponent's movements.

Without the aid of a coach it is often difficult for a player to be consistently alerted about incorrect movements or improper preparation. A player typically cannot observe their own movements and must rely on outcomes to judge whether a particular movement requires adjustment. In contrast, a third party observer, such as a coach, can observe and analyze a player's movements as they occur independent of the outcome achieved and therefore are able to provide feedback to the player quickly after the incorrect movement occurs. However, even if coaches are utilized, they must rely on their individual comprehension of proper movements and preparation to judge their observations of a player to provide appropriate corrective feedback. Because both comprehension and observation can vary from person-to-person, corrective feedback received from coaches can be highly subjective and inconsistently provided to the player, therefore detracting from the efficiency of the player's motor skill acquisition.

Additionally, such corrective feedback is limited to verbal commands or engaging a player in visual response drills, neither of which require an athlete to react to an actual opponent. Training drills of this type are not efficient at providing immediate feedback to a player. As a result, the training benefit of such drills is not as high as it could be if appropriate feedback and cue instruction could be supplied in real time.

Various devices in the prior art help to provide athletes with feedback about their motor movements. U.S. Pat. No. 5,681,993 discloses a plurality of force sensors disposed at predetermined pressure points between a human hand and a golf club. A conversion device transforms inputs from the force sensors into audible sound frequencies that vary in proportion to the force applied and the location of the force. The conversion device also transforms the force sensor inputs into vibratory outputs or electrical currents that vary in proportion to the force level and location of the force. The outputs can be useful to determine whether a club is being held correctly or if too much force is being applied to one portion of the club handle.

U.S. Pat. Nos. 5,439,217 and 5,439,216 each disclose a device that informs a player when a proper grip is being applied to a racket handle or golf club. The device utilizes a membrane switch that is connected to a portable power source and coupled to an audible alarm, which is activated when the switch closes. The alarm indicates when an excessive handle grip force is being applied to the handle.

U.S. Pat. No. 5,221,088 discloses a sports training aid having a pair of foot sensors that produce measurement signals corresponding to the weight applied to each foot sensor. The training aid compares the measurement signals with a specified range of values and produces audible sounds indicative of the relationship between the measurement signals and the specified range of values. The audible sounds provide the user with immediate feedback regarding shifts in weight.

U.S. Pat. No. 6,134,965 discloses a device for measuring the strike velocity of a tennis ball, where the device is installed on the tennis racket and measures the force exerted on the tennis racket strings during a ball strike. After a ball strike, the device displays a measured value associated with a calculated ball velocity.

There are additionally a variety of measuring devices for a striking element such as a racket or a golf club that are designed to measure the force with which a ball is struck or to measure the point of impact of a ball on the striking element. These devices are described in the following publications DE-A-34 36 218, U.S. Pat. Nos. 4,991,850, 4,870,868 and 4,008,324.

Some companies are developing devices that measure and record an athlete's movements during a tennis match. As an example, an Australian company called Smash Wearables Pty. Ltd. (see http://www.smashwearables.com) has developed a lightweight band that an athlete can wear on the wrist. The band, called "Smash," uses onboard sensors to transmit movement information to an application running on a Smartphone. The sensors measure specific physical values associated with movement of the athlete's wrist. The Smartphone application records the sensed physical values and calculates information about the movement of an implied (not directly connected) tennis racket. The calculated information can include racket speed, racket angle, racket momentum, the angle of wrist rotation, and the racket stroke trajectory. Based on the calculated information about the movement of a player's wrist, the Smartphone application can also infer a number of other attributes associated with a player's performance in a tennis match, including the number and type of shots (e.g., forehand versus backhand and topspin versus backspin), statistics about the amount of spin delivered across shots, and the consistency of racket placement at the point of impact with a tennis ball. Using the Smartphone application, an athlete can set certain performance goals and track progress toward those goals.

Similarly, the well-known tennis racket company, Babolat, sells a racket called the "Babolat Play Pure Drive" (see http://en.babolatplay.com/) which includes sensors integrated into the handle of the racket. The sensors measure and record information regarding power, impact location, and type and number of strokes. The information is stored in memory and later retrieved, analyzed, and presented to the user with a Smartphone application connected via USB or Bluetooth.

SUMMARY OF THE INVENTION

This brief summary is provided to introduce certain concepts in a simplified form that are further described below in the Detailed Description of the Embodiments. This brief summary is not intended to identify key features or essential features of the claimed subject matter, nor is it intended to limit in any way the scope of the claimed invention.

Embodiments of the present invention are directed to devices, systems, and methods for measuring values obtained from one or more sensors installed on a player's racket, paddle, or club (hereinafter, reference will generally be made to a "racket"), and/or worn on the player's body, and using those values to calculate a number of parameters, including those related to the physical position and motion of the racket. Embodiments of the present invention are also directed to devices, systems, and methods for receiving messages generated by other devices, including other embodiments of the present invention that are installed on rackets or worn on the bodies of other players. Embodiments of the present invention correlate the parameters and messages to generate real-time audible, visual, and/or haptic coaching prompts and other related commands and signals, for the purpose of improving certain motor skills associated with the corresponding sport.

In one embodiment, a device including a processor and one or more sensors is installed on a player's racket and/or on an article worn by the player. As the player swings the racket, the device measures values obtained from the one or more sensors and calculates various parameters associated with the racket's physical position and motion, including various angle measurements of the racket with respect to its position in space, the direction of motion, speed of motion, acceleration, vibration, and shock. The various parameters associated with a racket's physical position and motion may be further processed to determine when certain events have occurred or are in the process of occurring. These events can include forehand preparation, backhand preparation, overhead preparation, forehand swing, backhand swing, overhead swing, contact with a tennis ball, contact with another object (such as the net, the ground, or a player's body), and the application of spin to the ball. From such events, the embodiment can further derive one or more phases of a point or drill (such as serving, rallying, or ending a point).

Embodiments of the invention can determine if a racket has made contact with a ball and subsequently provide feedback to the player, for example as an audible alert or voice prompt emitted from the device or a connected peripheral. The invention can also transmit messages to other embodiments of the invention to trigger feedback in those embodiments. Further, the invention can transmit messages to a variety of peripherals to trigger other actions, such as triggering a ball machine to launch a ball or triggering a camera to capture a photo.

In one example, an embodiment of the invention can be used in a single-user mode where an audible alert or voice prompt is issued after the device detects a ball impact on the racket. A player can set a custom time delay (e.g., 1.5 seconds) between the moment of ball impact and the audible alert. Feedback provided to the player can indicate when the player should look up from the ball impact point. This feature trains the player to concentrate on the ball impact point on the racket and avoid a natural tendency to look up at the expected trajectory of the ball after impact, which pulls the shoulders and head forward and up prematurely, potentially causing a suboptimal hit.

While measuring and processing parameters relating to the physical position and motion of a racket, embodiments of the present invention may also be used in a multi-player mode. Such embodiments receive and process messages generated by other embodiments of the invention (for example, embodiments used by an opponent), and issue audible coaching prompts to a player, in real time, under certain pre-programmed conditions, with the goal of improving the player's performance by revisiting the cognitive and associative stages of motor learning and by conditioning and reinforcing specific physical behaviors through repetition. For example, the feedback can indicate when the player should make a specific action, for example to assess his/her level of preparedness or to move his/her body and racket to a ready position such as a "split step" position. The prompt can also warn a player when to prepare for a backhand or a forehand shot. This feature trains the player to prepare earlier and make use of the full amount of time available between volleys. The audible coaching prompts can include sounds, such as beeps or other tones, as well as prerecorded or synthesized verbal instructions. The prompts can be provided directly to the player or to another player or observer via wireless communications.

In another example, a message transmitted by an embodiment of the invention can be received by an embodiment connected to or integrated within a ball machine. Such a message can trigger the ball machine to launch a new ball. The timing of the launch can be similar to a return shot from a real player, thereby simulating a more realistic environment during practice. The embodiment connected to or integrated within the ball machine can also send messages to other embodiments, such messages including information about the launch, including power, spin, and direction. This information enables the other embodiments to generate feedback that is appropriate for the particular situation.

Finally, in still another example, a message transmitted by an embodiment of the invention can be received by other external devices. For example, a camera can receive messages from the embodiment that instruct the camera to take a photo, a series of photos, or a video immediately upon receiving the message or a user-adjustable time after the message is received. The resulting pictures or videos can then be used retrospectively to analyze and improve a player's preparation and execution.

Over time and through repetition, the varied timing prompts provided by embodiments of the invention should help to improve the player's skill level by training the player to become better at recognizing certain opponent behaviors, to improve the performance of certain movements, and to reinforce the timing and execution of various combinations of movements in reaction to those of a vigorous opponent.

DESCRIPTION OF THE EMBODIMENTS

Figure 1A:
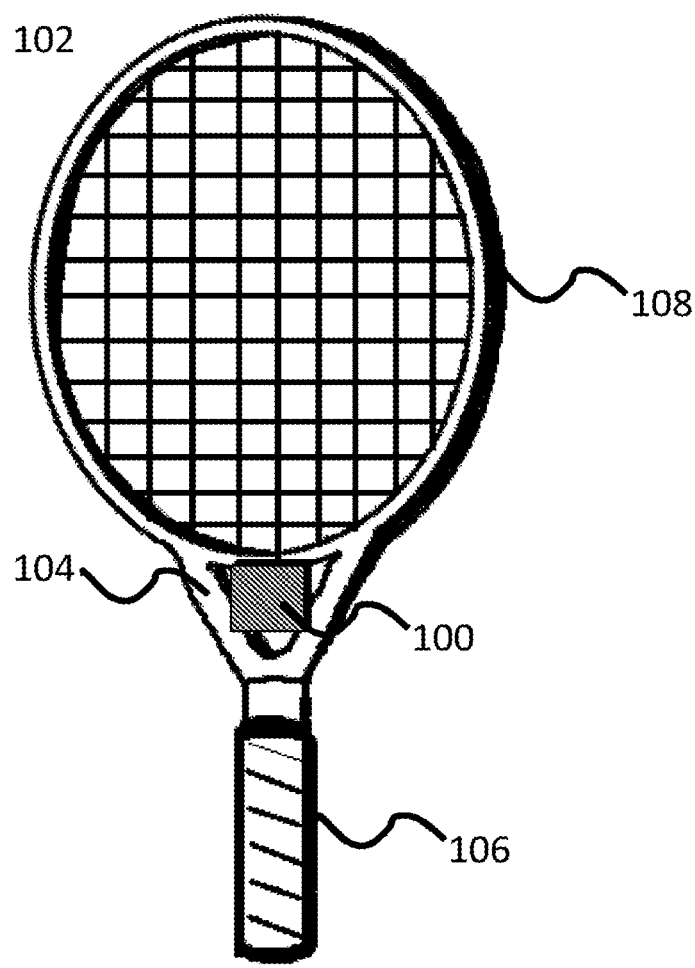
FIG. 1A illustrates a tennis racket installed with an exemplary embodiment of a device for sensing racket motion parameters and providing feedback in accordance with the present invention.

Embodiments of the present invention will be described with reference to the accompanying drawings, wherein like parts are designated by like reference numerals throughout, and wherein the leftmost digit of each reference number refers to the drawing number of the figure in which the referenced part first appears. The terms "player" and "user" are used interchangeably throughout the description, and both should generally be treated as a user of the present invention.

FIG. 1A is a view of a tennis racket installed with an embodiment of a device for sensing racket position and motion parameters and providing feedback in accordance with the present invention. The embodiment provides a coaching device 100 installed on a tennis racket 102. As illustrated, coaching device 100 is installed in the throat 104 of tennis racket 102, i.e. in the opening between the two beams of the racket that extend from the handle 106 to the head 108. Coaching device 100 can be attached to any part of racket 102 in a variety of ways including, for example, through the use of one or more clips, bolts, straps, bands, clamps, magnets, adhesives, or a combination thereof. In an embodiment, coaching device 100 includes a body constructed of a suitably strong but lightweight material (e.g., plastic or aluminum), and the body houses a plurality of components described in further detail below. Coaching device 100 can also be embedded within racket 102. For example, coaching device 100 can be embedded within handle 106. Alternatively, if the throat of tennis racket 102 is a solid component, coaching device 100 can be embedded within the solid throat.

Figure 1B:
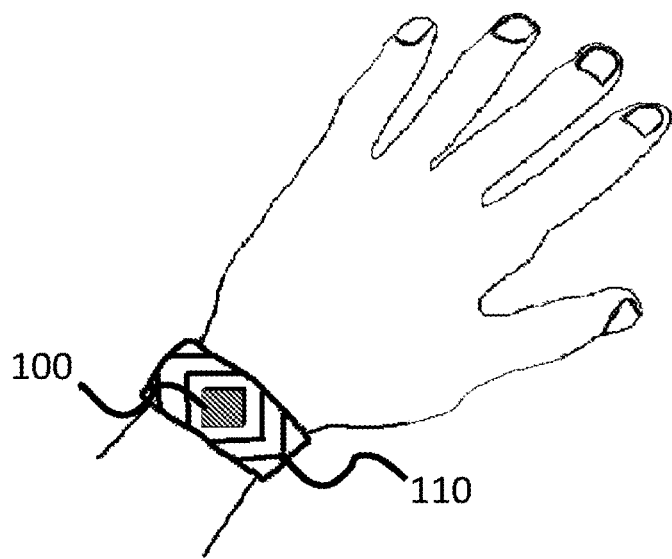
FIG. 1B illustrates a wearable device installed with an exemplary embodiment of a device for sensing racket motion parameters and providing feedback in accordance with the present invention.

FIG. 1B is a view of a wearable accessory 110 installed with another embodiment of the present invention. The embodiment provides coaching device 100 installed on (e.g., via one or more clips, bolts, straps, bands, clamps, magnets, adhesives, or a combination thereof) or embedded within wearable accessory 110. Wearable accessory 110 can be any sort of accessory that is wearable on a player's hand or wrist, for example a bracelet, wristband, or glove. Wearable accessory 110 can be made of any suitable material, including textile, leather, metal, plastic, rubber, wood, or a combination thereof.

Figure 1C:
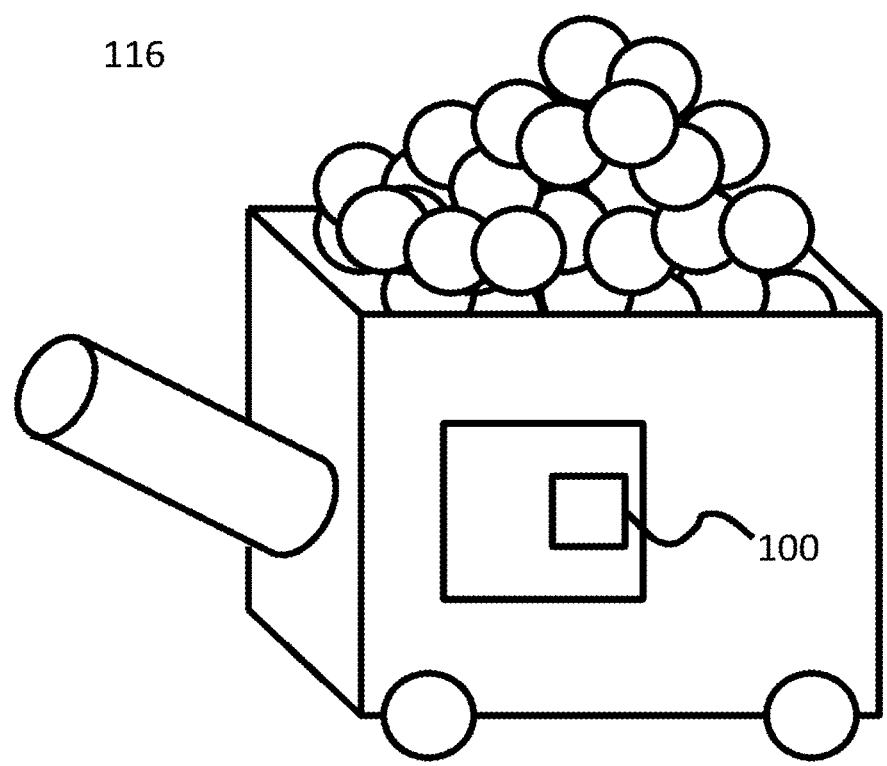
FIG. 1C illustrates a ball machine installed with an exemplary embodiment of a device for triggering the ball machine to launch balls in response to events detected at a racket in accordance with the present invention.

FIG. 1C is a view of a ball machine 116 installed with another embodiment of the present invention. The embodiment provides coaching device 100 connected to ball machine 116 via wired or wireless means according to well-known connection methods. Coaching device 100 can also be integrated within ball machine 116. In such an embodiment, coaching device 100 can share one or more components with ball machine 116, for example the ball machine's power supply. Ball machine 116 can be any type of ball machine, for example a tennis ball machine, a table tennis ball machine, or a baseball or softball pitching machine. These and other embodiments will be described in further detail below.

Figure 2:
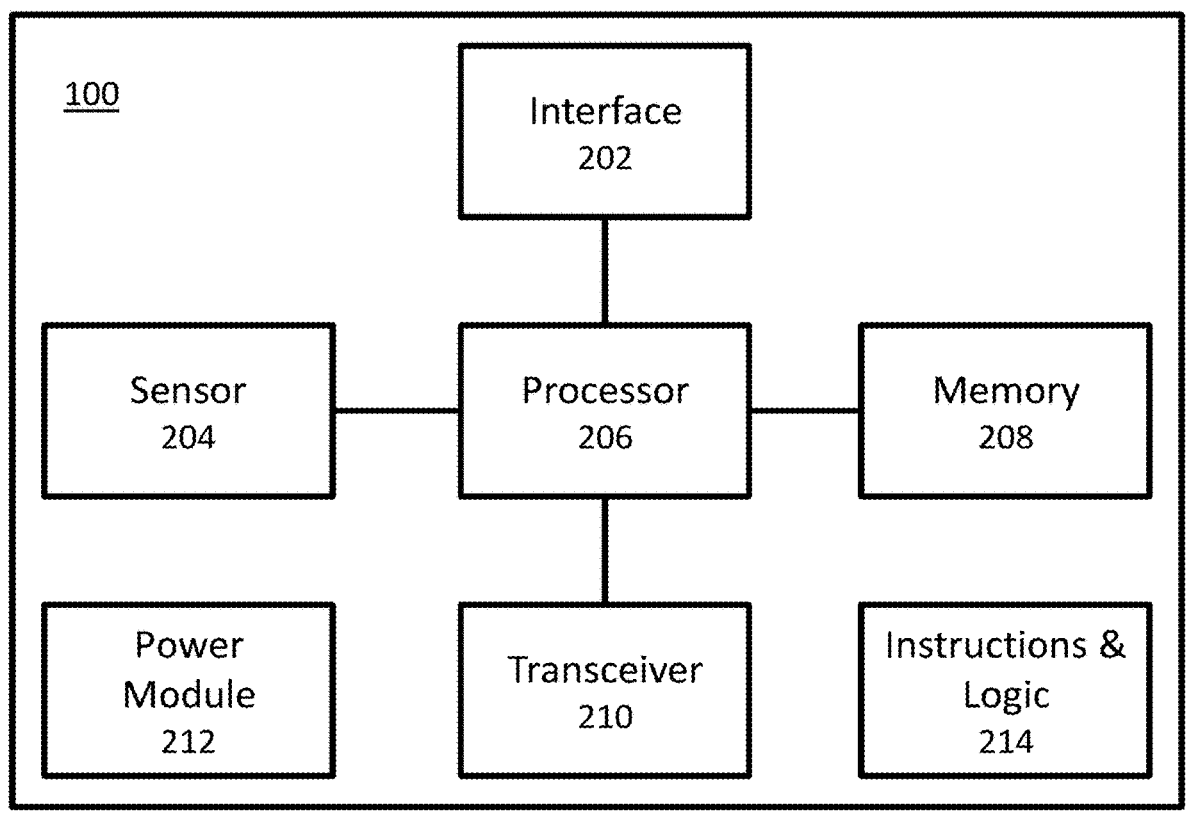
FIG. 2 is a block diagram of certain internal components of an exemplary embodiment of a device for sensing racket position and motion parameters and providing feedback in accordance with the present invention.

FIG. 2 is a block diagram of an exemplary embodiment of coaching device 100 in accordance with the present invention, which in certain operative embodiments can be installed on a racket 102 as illustrated in FIG. 1A, installed on a wearable accessory 110 as illustrated in FIG. 1B, or installed on a combination of the two. In such a combination, for example, some components may be installed on the racket 102, other components may be installed on the wearable accessory 110, and the components may share information via wireless communications. In the embodiment of FIG. 2, coaching device 100 comprises numerous components, including one or more interface(s) 202, one or more sensor(s) 204, one or more processor(s) 206, one or more memory(ies) 208, one or more transceiver(s) 210, one or more power module(s) 212, and instructions and logic 214.

Interface 202 may comprise one or more devices for receiving input or providing output. Interface 202 can include one or more digital display(s) for outputting a text-based or graphical user interface and for receiving user input, for example via a touchscreen component. Interface 202 can also include one or more physical buttons, scroll wheels, or other conventional devices for receiving user input. In an embodiment, a player may use interface 202 to configure coaching device 100, toggle power, adjust volume, switch between various modes of operation, review metric data, and otherwise interact with coaching device 100.

In an embodiment, interface 202 includes a microphone for receiving voice commands or messages. A player may, for example, use voice commands as an alternative to or in addition to using a digital display and/or buttons for interacting with coaching device 100. A microphone may also be used to record voice messages that may be sent to other embodiments of the invention.

Interface 202 may comprise one or more devices for providing coaching feedback to the player. For example, interface 202 can include one or more light(s) (e.g., light emitting diodes) for providing visual feedback and/or one or more loudspeaker(s) for providing audible feedback. Interface 202 may also comprise one or more vibration motors for providing haptic feedback to the player. For example, a vibration motor like those typically found in modern mobile phones may be instructed to vibrate or "rumble" to remind a player to recover and prepare for the next shot. In embodiments, coaching feedback may be provided by any combination of one or more of the feedback devices disclosed herein.

Sensor 204 may comprise one or more device(s) for detecting and measuring a variety of physical parameters associated with coaching device 100. For example, sensor 204 can include one or more accelerometer(s) for measuring one or more of the orientation, coordinate acceleration, vibration, and shock affecting coaching device 100. Sensor 204 can include any type of sensor that is capable of detecting and/or measuring physical/spatial parameters, including vibration, acceleration, and direction of motion. For example, a gyroscope may be used instead of or in addition to an accelerometer to measure the orientation of coaching device 100.

Processor 206 may comprise one or more devices for executing machine-readable instructions that perform one or more predetermined tasks. Processor 206 can comprise any one or a combination of hardware, firmware, and/or software. In general, processor 206 can utilize mechanical, pneumatic, hydraulic, electrical, magnetic, optical, informational, chemical, and/or biological principles, signals, and/or inputs to perform tasks. In certain embodiments, processor 206 can act upon information by manipulating, analyzing, modifying, converting, or transmitting the information for use by an executable procedure and/or an information device, and/or routing the information to an output device. Processor 206 can function as a central processing unit, local controller, remote controller, parallel controller, and/or distributed controller, etc. Processor 206 can include a general-purpose device, such as a microcontroller and/or a microprocessor. In certain embodiments, processor 206 can be a dedicated purpose device, such as an Application Specific Integrated Circuit (ASIC) or a Field Programmable Gate Array (FPGA) that has been designed to implement in its hardware and/or firmware at least a part of an embodiment disclosed herein.

Memory 208 can be any type of apparatus known in the art that is capable of storing analog or digital information such as instructions and/or data. Examples include a non-volatile or read only memory ("ROM"), volatile or random access memory ("RAM"), flash memory, various types of magnetic media, and the like. Memory 208 can be coupled to one or more processor(s) 206 and can store instructions and logic adapted to be executed by one or more processor(s) 206, as according to any of the embodiments disclosed herein.

Transceiver 210 may comprise any device, system, subsystem, or component capable of wirelessly transmitting and/or receiving information, particularly messages sent to or received from other coaching devices 100 in accordance with embodiments of the present invention. For example, transceiver 210 can include a cellular radio, RF transceiver, Bluetooth transceiver, WiFi transceiver, wireless broadband transceiver (WiMAX), ZigBee transceiver, or other similar capability.

Transceiver 210 may also receive input and provide output or feedback to one or more external device(s), including ball machines, cameras, headsets, computers, tablets, mobile phones, memory sticks, and other electronic devices. For example, transceiver 210 can provide output to a camera, the output triggering the camera to record a picture or video corresponding to an event occurring on coaching device 100. In another example, transceiver 210 can provide output to and receive input from a mobile phone, wherein the mobile phone permits a player to review metric data recorded by coaching device 100 and configure coaching device 100. The connection between transceiver 210 and an external device can be wireless or wired. For wired connections, transceiver 210 can include one or more port(s) accessible on or within the housing of coaching device 100.

Power module 212 may comprise one or more devices for providing electrical power to the other components of coaching device 100. Power module 212 may include one or more battery cells (e.g., lithium, alkaline, or NiMH battery cells) or other power supplies, any number of which can be electrically connected together. Some or all of the battery cells may be rechargeable. Power module 212 may also include a power input to receive input power from a power source, and a power output to provide output power to a load. In an embodiment, power module 212 stores kinetic energy captured from the motion of coaching device 100 as electricity in one or more battery cell(s) and/or capacitor(s).

Instructions and logic 214 may comprise directions adapted to cause a machine, such as coaching device 100, to perform one or more particular activities, operations, or functions. The directions, which can sometimes form an entity called a "kernel", "operating system", "program", "application", "utility", "subroutine", "script", "macro", "file", "project", "module", "library", "class", "object", or "Application Programming Interface," etc., can be embodied as machine code, source code, object code, compiled code, assembled code, interpretable code, and/or executable code, etc., in hardware, firmware, and/or software. Instructions and logic 214 may reside in processor 206, in memory 208, or in another specialized device or component.

For ease of illustration, other components common to electrical devices have been excluded from FIG. 2. For example, a communications bus permits each of the other components to communicate with each other according to well-known techniques.

Having described the components of coaching device 100, attention will now be paid to its operation. For purposes of this description, reference will be made to the following terms:

Physical Event: a measurable occurrence in the physical world (e.g., a swing of a racket or an impact with a ball). A Physical Event may indicate the occurrence of one or more Tennis Events.

Tennis Event: a logical occurrence derived from one or more Physical Events (e.g., the start of a point). A Tennis Event may trigger one or more Notifications and/or Calculations.

Notification: an instruction to take some action corresponding to one or more Tennis Events (e.g., an instruction to play a recorded voice message coaching the player to focus on the point of impact).

Calculation: an instruction to calculate and/or output one or more metrics corresponding to one or more Tennis Events (e.g., an instruction to tally the number of shots in a rally).

As discussed above, coaching device 100 measures values obtained from sensor 204 and calculates one or more physical parameters associated with coaching device 100. Coaching device 100 then translates these parameters into one or more Physical Events. The translation process may be specified by instructions and logic 214 and performed by processor 206. More particularly, instructions and logic 214 may include one or more tables that map certain parameters to one or more Physical Events. For example, parameters consistent with a forehand swing may map to one Physical Event, while parameters consistent with striking a ball three times in quick succession may map to a different Physical Event.

A Physical Event may be any occurrence (or, in some embodiments, a pause between occurrences) that may be derived from measurements taken by sensor 204. For example, Physical Events can include an impact of the player's racket with a tennis ball, timed pauses between impacts, multiple closely spaced impacts, the number of steps between impacts, a physical orientation of the racket, and an acceleration of the racket.

For purposes of illustration only, an embodiment is described that includes the following specific Physical Events: Local Impact (i.e., the player strikes the ball), Remote Impact (i.e., the player's opponent strikes the ball), No Impact Swing (i.e., a swing and miss of the ball), First Pause (i.e., a pause long enough to indicate that a point or exchange has ended), Second Pause (i.e., a pause long enough after the First Pause to indicate that the next point or exchange is about to begin), Triple Local Impact (i.e., the player is preparing to serve), and Triple Remote Impact (i.e., the player's opponent is preparing to serve). Other Physical Events may be contemplated by one of ordinary skill in the art without departing from the scope of the invention, provided they can be mapped to one or more values and parameters.

From each Physical Event, coaching device 100 derives a corresponding Tennis Event. A Tennis Event can include any distinct event that can occur during a tennis point or drill (e.g., serve, shot, end of point, etc.). For purposes of illustration only, an embodiment is described that includes the following specific Tennis Events: Start of Exchange, My Serve, Opponent's Serve, My Shot, Opponent's Shot, and End of Exchange. Other Tennis Events may be contemplated by one of ordinary skill in the art without departing from the scope of the invention.

As illustrated in Table 1, each Physical Event maps to at least one Tennis Event according to a logical correlation. In an embodiment, a single Physical Event may map to different Tennis Events depending on an operating mode of coaching device 100, such as a Drill Mode or a Point Mode. For example, when Point Mode is operational, a Triple Impact Physical Event indicates that the player is about to begin his or her serve and therefore maps to a Start of Point Tennis Event. A player may select an operating mode by, for example, interacting with a graphical user interface and/or one or more physical buttons provided by interface 202, or any other suitable means such as by issuing voice commands.

TABLE 1

| Physical Event | Corresponding Tennis Event | |
|---|---|---|
| | Drill Mode | Point Mode |
| Local Impact | My Shot | if first impact, My Serve, else My Shot |
| Remote Impact | Opponent's Shot | if first impact, Opponent's Serve, else Opponent's Shot |

TABLE 1-continued

| | Corresponding Tennis Event | |
|---|---|---|
| Physical Event | Drill Mode | Point Mode |
| No Impact Swing | End of Exchange | End of Point |
| First Pause | End of Exchange | End of Point |
| Second Pause | Start of Exchange | Start of Point |
| Triple Impact | Start of Exchange | Start of Point |

Tennis Events drive a computerized model of a tennis drill or point. In an embodiment, the computerized model may comprise a finite state machine. A finite state machine ("FSM") comprises a number of states, and the FSM is only ever in one state at a time (i.e., the "current state"). The FSM transitions from one state to another upon the occurrence of a triggering event or condition. In an embodiment, each state in the FSM corresponds to a phase of a tennis drill or point, and the occurrence of a Tennis Event causes the FSM to either transition to a different state or repeat the same state.

Each state in the FSM may further be associated with one or more Notifications and/or one or more Calculations as defined above. In an embodiment, a Notification includes user-customizable coaching feedback. The coaching feedback can include audible feedback (e.g., tones, recorded voice messages, and/or other sound effects), visual feedback (e.g., textual or graphical messages and/or flashing LEDs), haptic feedback (e.g., vibrations), or any combination of the above. For example, a variety of methods may be used to encourage a player to keep his or her eyes focused on the point of contact between the racket and the ball. In an embodiment, a Notification includes switching on an LED for a short period of time with the occurrence of a My Shot Tennis Event to remind the player to remain focused on the point of contact. In the same or an alternative embodiment, a Notification includes playing a recorded voice message shortly after the occurrence of a My Shot Tennis Event, thereby reminding the player to stay focused on the point of contact during the next shot.

Any of a variety of recorded voice messages may be played as part of a Notification without departing from the scope of the invention. In an embodiment, the voice messages may be predefined and recorded by a well-known tennis professional, and/or the voice messages may be recorded by the player or the player's coach. Some example voice messages may include the following: "Keep feet moving," "Recover and split," "Turn shoulders," "Move through the shot," and "Point to the ball."

A Calculation can be any instruction to calculate and/or output (e.g., via a GUI or audible message) one or more metrics corresponding to one or more Tennis Events. For example, metrics can include one or more of the following: number of shots in a rally or point, length of time of a rally or point, transit time for a player's shot, time between shots, swing speed, power, number of steps between shots, and statistical analyses of any of the above (e.g., averages, totals, etc.). Other metrics may be contemplated by one of ordinary skill in the art without departing from the scope of the invention.

For example, an End of Point Tennis Event may cause a Calculation that outputs the number of shots in the most recent point. A player may also review metrics on demand, for example by using interface 202 to select a particular Calculation.

In an embodiment, there may be different FSMs associated with different operating modes. For example, FIGS. 3 and 4 illustrate the phases of two FSMs when coaching device 100 is operating in a Drill Mode and a Point Mode respectively.

Figure 3:
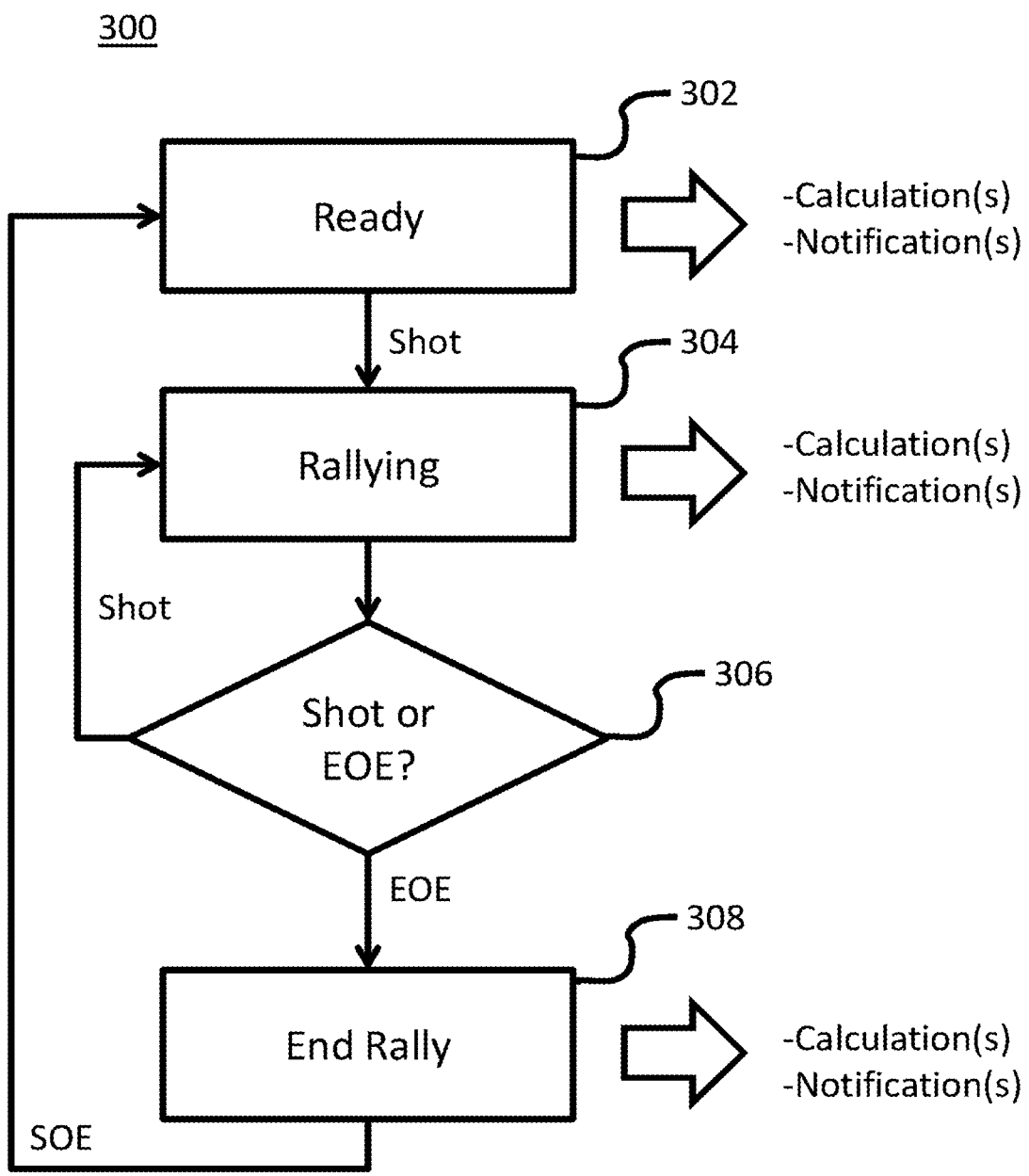
FIG. 3 is a flow chart that is representative of an exemplary embodiment of a finite state machine for associating events detected at a racket with phases of a point or drill.
Figure 4:
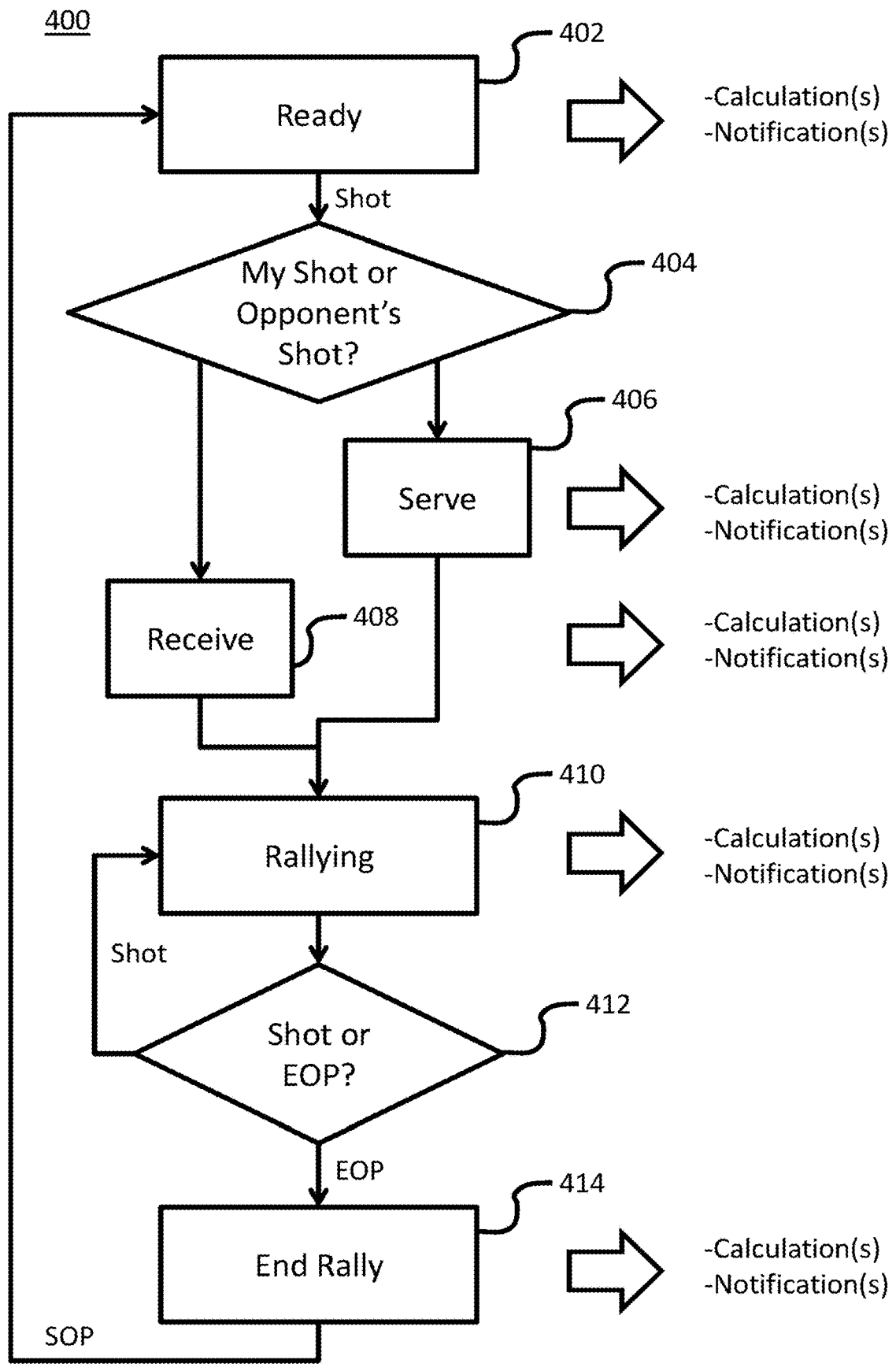
FIG. 4 is a flow chart that is representative of an exemplary embodiment of a finite state machine for associating events detected at a racket with phases of a point or drill.

FIG. 3 illustrates FSM 300 for a Drill Mode embodiment. FSM 300 first enters phase 302 (a ready state or starting state) with the occurrence of a Start of Exchange ("SOE") Tennis Event. Phase 302 may be associated with one or more Calculations and/or Notifications. For example, a Calculation may include setting a shot count value to zero, and a Notification may include outputting audible feedback instructing the player to assume a ready stance.

In the embodiment illustrated in FIG. 3, a Local Impact or Remote Impact Physical Event may trigger a corresponding My Shot or Opponent's Shot Tennis Event, and thus cause FSM 300 to enter phase 304 (a rallying state). Like with phase 302, phase 304 may be associated with one or more Calculations and/or Notifications. For example, a Calculation may include incrementing a shot count, and a Notification may include outputting a recorded voice message instructing the player to maintain a neutral grip.

FSM 300 repeats phase 304 each time a My Shot or Opponent's Shot Tennis Event occurs at decision 306, and enters phase 308 (end of rally) if an End of Exchange ("EOE") Tennis Event occurs at decision 306. Phase 308 may also be associated with one or more Calculations and/or Notifications. For example, a Calculation may include outputting the total shot count, and a Notification may include audible feedback offering encouragement to the player, or there may be no corresponding Calculation or Notification at all. FSM 300 loops back to phase 302 with the occurrence of an SOE Tennis Event.

In an embodiment, Calculations and Notifications are associated with phases of an FSM in a manner that is instructive and relevant to the player's actions. For example, it would be of little use to output an audible Notification concerning a serve during a rallying phase. Calculations and Notifications may be configured to particular phases of an FSM in a predefined manner, or the player may customize the configurations. Such configurations of Calculations and Notifications may be saved as Lesson Plans that are quickly selectable and modifiable by the player. In an embodiment, coaching device 100 includes a default lesson plan for each operating mode.

A Lesson Plan is a configuration of Calculations and Notifications. In an embodiment, coaching device 100 may have one or more default Lesson Plans and a player may create and edit his or her own lesson plans. Many different embodiments of a Lesson Plan are contemplated by the invention, but Table 2 illustrates a sample Lesson Plan, including a name, operating mode, voice selection, and a plurality of Calculation and Notification parameters and their corresponding Tennis Events. Lesson Plans may also include a variety of other parameters.

TABLE 2

| Lesson Plan Parameters | |
|---|---|
| Lesson Plan Name: | "Solid Rallying" |
| Play Mode: | "Drill" |
| Voice: | Default |

| Calculation/Notification Parameters | | |
|---|---|---|
| Tennis Event | Calculations | Notifications |
| My Shot | Tally Shot Count: On<br>Record Swing Speed: On | Announce: {"recover and split," "keep feet moving"}; |

TABLE 2-continued

Lesson Plan Parameters

| | | |
|---|---|---|
| | Record Impact Point: Off | Delay: 0.25 secs;<br>Order: Random;<br>Frequency: Every 3rd shot; |
| Opponent's Shot | Tally Shot Count: On | Announce: {"step into shot," "80% power"};<br>Delay: 0.25 secs;<br>Order: Default;<br>Frequency: Randomly every 3 shots; |
| End of Exchange | Announce: {Shot Count, Avg. Swing Speed, Avg. number of steps between shots};<br>Delay: 0 secs<br>Order: Default;<br>Frequency: Every time | None |
| Start of Exchange | Reset Shot Count: On | None |

In an embodiment, Calculations and Notifications may also be configured to execute instantaneously upon the occurrence of a Tennis Event, or they may be configured to execute according to a predefined and/or user-configurable amount of delay. For example, a Notification that is intended to instruct a player on his or her next shot may execute N seconds after the current shot, where N is a user-configurable number of seconds and/or partial seconds. In an embodiment, the invention automatically adjusts the amount of the delay based on a calculated metric of the average time between shots. In this manner, the invention will automatically adapt to tennis players of all skill levels.

In an embodiment where more than one Calculation and/or Notification is configured to execute with a particular phase, the player may configure the order in which the Calculations and/or Notifications execute. The order can be randomized or fixed. In an embodiment, only a subset of the available Calculations and/or Notifications associated with a particular phase is executed, the subset being selected randomly (e.g., select two out of an available ten) and/or according to a schedule (e.g., where some Calculations and/or Notifications are executed every Nth time). In this manner, the player may receive a variety of coaching feedback, thereby allowing him or her to focus on multiple areas of improvement.

FIG. 4 illustrates FSM 400 for a Point Mode embodiment. Phases 402, 406, 408, 410, and 414 may be associated with one or more Calculations and/or Notifications as discussed above. FSM 400 enters phase 402 (a ready state or starting state) with the occurrence of a Start of Point ("SOP") Tennis Event. At decision 404, FSM 400 transitions to phase 406 (a service state) upon the occurrence of a My Shot Tennis Event or phase 408 (a receiving state) upon the occurrence of an Opponent's Shot Tennis Event. From either of phases 406 or 408, FSM 400 enters phase 410 (a rallying state) upon the occurrence of a My Shot or Opponent's Shot Tennis Event.

FSM 400 repeats phase 410 each time a My Shot or Opponent's Shot Tennis Event occurs at decision 412, and enters phase 414 (end of rally) if an End of Point ("EOP") Tennis Event occurs at decision 412. FSM 400 then loops back to phase 402 with the occurrence of an SOP Tennis Event.

Coaching device 100 may be used in single-user embodiments or multi-user embodiments. In single-user embodiments, Tennis Events at a single coaching device 100 drive a corresponding FSM such as FSM 300. Each state in FSM 300 may be triggered by Tennis Events at a single coaching device 100.

In multi-user embodiments, each coaching device 100 maintains its own FSM (e.g., a FSM 300 or FSM 400), but the FSM may be affected by Tennis Events at other coaching devices 100. For example, two coaching devices may each be executing FSM 400, and both begin in the ready phase 402. When a My Shot Tennis Event occurs at one coaching device 100, it will wirelessly transmit the My Shot Tennis Event to the other coaching device 100 (e.g., via its transceiver 210) where it will be received and interpreted as an Opponent's Shot Tennis Event. In other words, each coaching device 100 transmits each Tennis Event to each other coaching device 100, thereby ensuring that the FSMs at each coaching device 100 are synchronized.

In an embodiment, Tennis Events are transmitted in the form of messages, and each message includes an identification of the coaching device transmitting the message along with information about the Tennis Event. Such information may include the type of Tennis Event (e.g., a "My Shot" Tennis Event) as well as information about the type of shot (e.g., speed, spin, direction, etc.). For example, a coaching device 100 may determine that a player hit a forehand lob shot based on the speed and direction of the shot (e.g., as measured by sensor 204), and the corresponding message may include this information, thereby enabling a receiving coaching device 100 to generate a relevant Notification (e.g., an announcement to prepare for an overhead shot).

In alternative embodiments, messages may include measurement information gathered directly from sensor 204 and/or information about a Physical Event instead of or in addition to information about the Tennis Event. In such embodiments, the receiving coaching device 100 translates the measurement information into Physical Events and derives corresponding Tennis Events in the same manner as the transmitting device.

In multi-user embodiments, coaching device 100 may also operate according to a singles player mode or a doubles player mode. For example, two opponents in a singles match may each configure their respective coaching devices 100 to operate in a singles player mode, meaning alternating shots are expected by the FSM (e.g., a My Shot Tennis Event followed by an Opponent's Shot Tennis Event). Two teammates in a doubles match, on the other hand, may each configure their respective coaching device 100 to operate in a doubles player mode, meaning that only one shot per team is expected by the FSM. For example, when two teammates are operating coaching devices 100 in a doubles player mode, the FSM 400 at each coaching device 100 will recognize a My Shot Tennis Event regardless of which player hits the ball.

In multi-user embodiments, two or more coaching devices 100 establish a communication session using a conventional "handshake" or other suitable discovery/connection mechanism. For example, a player using one coaching device 100 may initiate a discover function at coaching device 100 that seeks out other coaching devices 100 broadcasting their availability. Password authentication or other suitable mechanisms may be employed to ensure that only authorized coaching devices 100 may join a communication session.

Figure 5A:
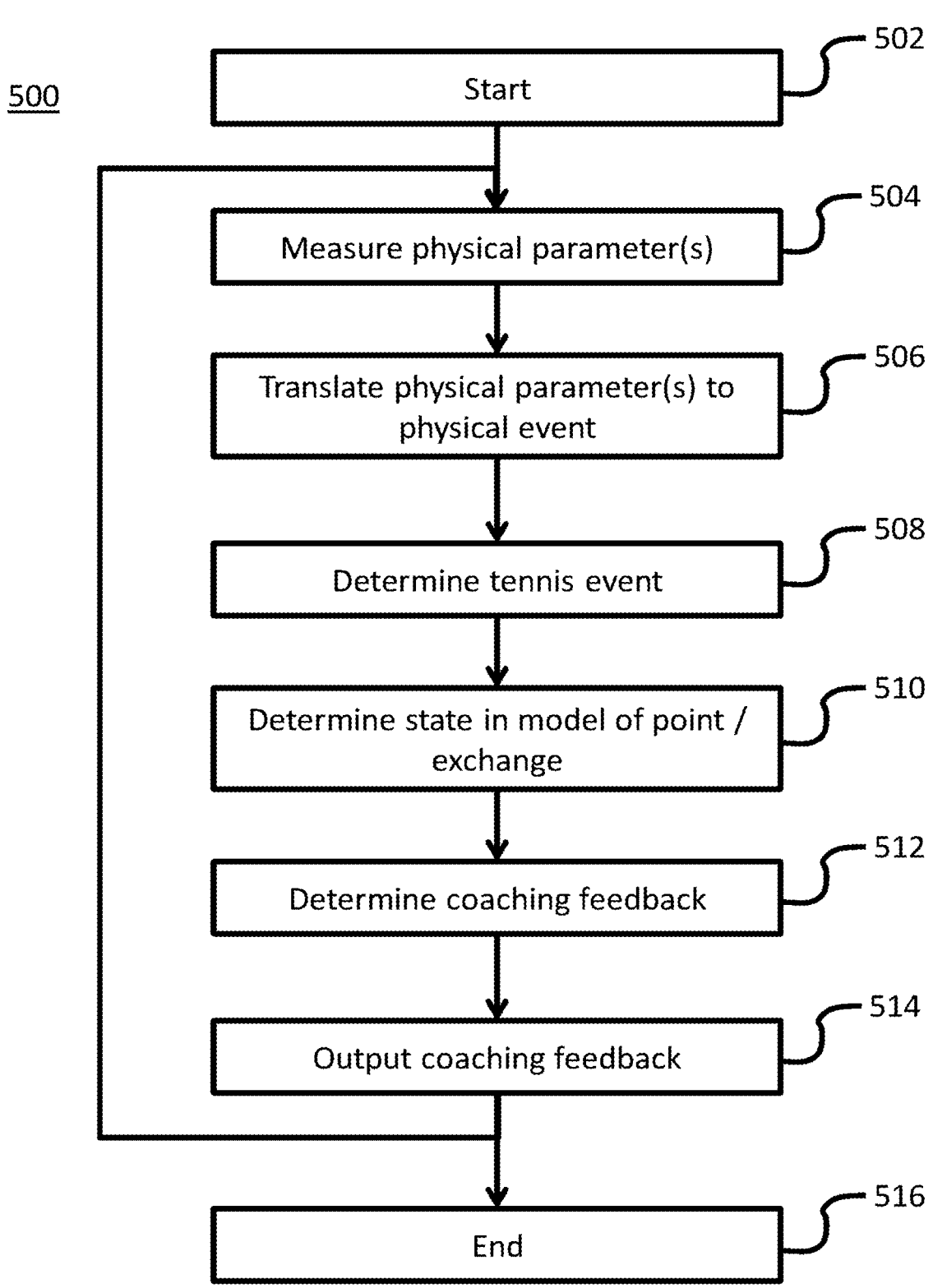
FIG. 5A illustrates an exemplary single-user embodiment of a method for providing feedback in accordance with the present invention.
Figure 5B:
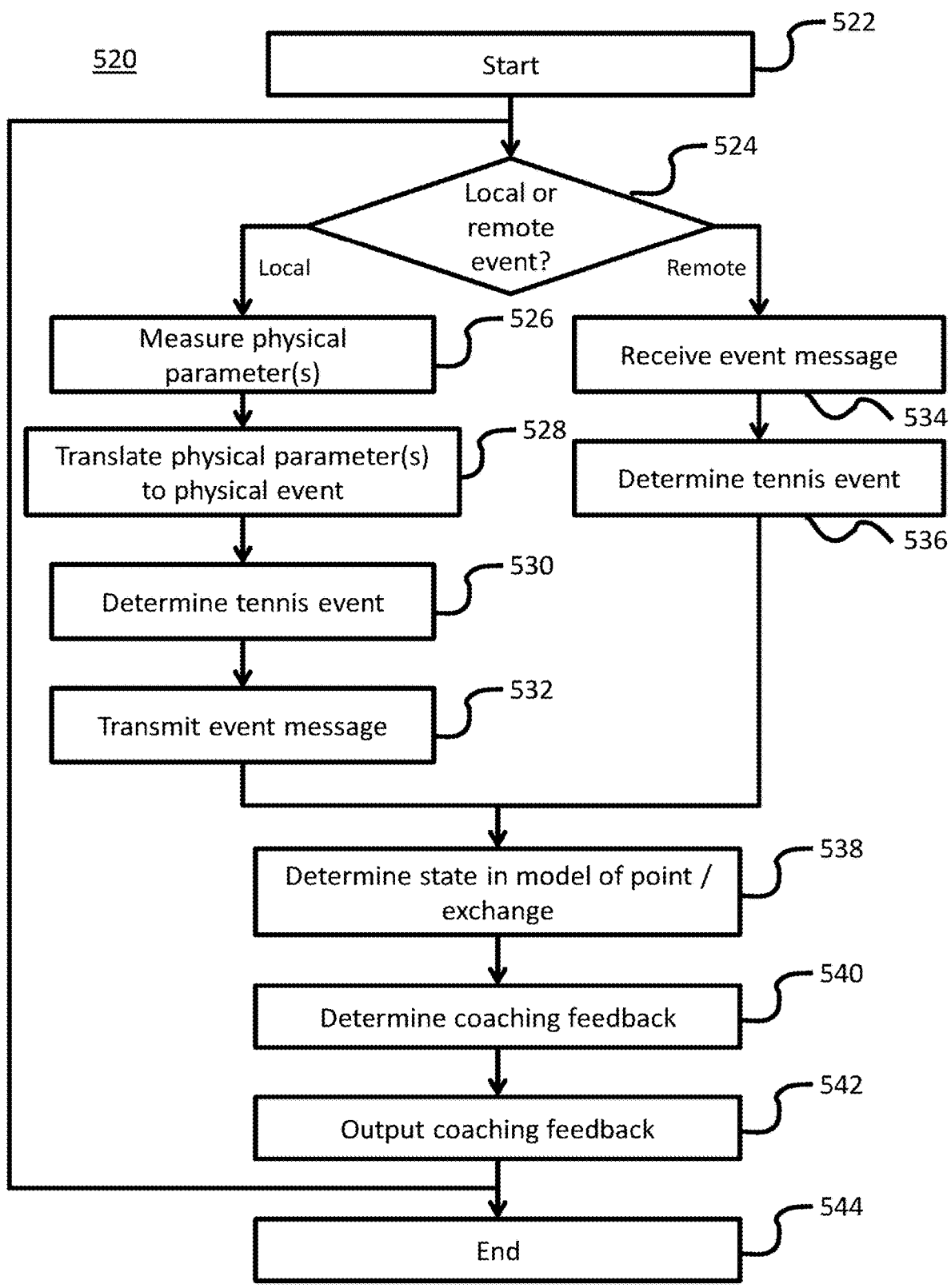
FIG. 5B illustrates an exemplary multi-user embodiment of a method for providing feedback in accordance with the present invention.

FIGS. 5A and 5B respectively illustrate a single-user method 500 and a multi-user method 520 for providing feedback in accordance with the present invention. Method 500 begins at step 502. A player may, for example, initiate method 500 by powering on his or her coaching device 100 and selecting a drill or point mode. At step 504, coaching device 100 measures values obtained from sensor 204 and calculates one or more physical parameters (e.g., parameters corresponding to the position and/or motion of the player's racket). At step 506, coaching device 100 translates the physical parameters into a Physical Event (e.g., a swing of a racket or an impact with a ball). At step 508, coaching device 100 determines a Tennis Event (e.g., the start of a point) based on the Physical Event in the previous step. At step 510, coaching device 100 determines a corresponding state (e.g., a rallying state) in a model (e.g., a finite state machine) of a drill or point based on the Tennis Event in the previous step. At step 512, coaching device 100 determines coaching feedback (e.g., a Notification and/or a Calculation) that corresponds to the determined state in the previous step. At step 514, coaching device 100 outputs the coaching feedback (e.g., via one or more of audible, visual, and haptic feedback). Finally, if the player finishes a drill or game or wishes to switch to a different mode, method 500 ends at step 516. Otherwise, method 500 returns to step 504.

Method 520 begins at step 522. As with method 500, a player may, for example, initiate method 520 by powering on his or her coaching device 100 and selecting a drill or point mode. At step 524, coaching device 100 either detects a local event (e.g., an event detected at the player's racket) or a remote event (e.g., an event received from the player's opponent). For local events, at step 526, coaching device 100 measures values obtained from sensor 204 and calculates one or more physical parameters (e.g., parameters corresponding to the position and/or motion of the player's racket). Then, at step 528, coaching device 100 translates the physical parameters into a Physical Event (e.g., a swing of a racket or an impact with a ball). At step 530, coaching device 100 determines a Tennis Event (e.g., the start of a point) based on the Physical Event in the previous step. At step 532, coaching device transmits an event message based on the Tennis Event to another embodiment of the invention.

For remote events, at step 534, coaching device 100 receives an event message from another embodiment of the invention. At step 536, coaching device 100 determines a Tennis Event (e.g., the start of a point) based on the event message received in the previous step.

For both local and remote events, at step 538, coaching device 100 determines a corresponding state (e.g., a rallying state) in a model (e.g., a finite state machine) of a drill or point based on the Tennis Event in one of step 532 or step 536. At step 540, coaching device 100 determines coaching feedback (e.g., a Notification and/or a Calculation) that corresponds to the determined state in the previous step. At step 542, coaching device 100 outputs the coaching feedback (e.g., via one or more of audible, visual, and haptic feedback). Finally, if the player finishes a drill or game or wishes to switch to a different mode, method 520 ends at step 544. Otherwise, method 520 returns to step 524.

As illustrated in FIG. 1C, embodiments of coaching device 100 may interface with a ball machine 116. In such an embodiment, one or more players with coaching devices 100 may practice with a ball machine 116 as if they were playing or practicing with a human opponent or coach. A coaching device 100 connected to a ball machine 116 maintains an FSM in the same manner as a coaching device 100 used by a player. In essence, a coaching device 100 connected to a ball machine can be thought of as a coaching device 100 used by another player in a multi-user embodiment, i.e., it transmits and receives messages concerning Tennis Events and other related information, and such Tennis Events drive a corresponding FSM. The primary difference is that Notifications trigger actions at the ball machine (e.g., launching the next ball) instead of outputting coaching feedback.

For example, a player with a coaching device 100 may initiate a Start of Exchange Tennis Event by hitting her racket with her hand three times. The player's coaching device 100 will then transmit the Start of Exchange Tennis Event to the ball machine's 116 coaching device 100 where a corresponding Notification will trigger the ball machine 116 to launch a ball. A rally between the player and the ball machine 116 may then proceed according to an FSM (e.g., FSM 400), with each of the player's shots being interpreted as an Opponent's Shot Tennis Event and triggering a Notification and subsequent launch of another ball at ball machine 116.

Various parameters at ball machine 116 may be user-configured or established in pre-defined lesson plans designed for ball machine 116. For example, ball machine 116 may be configured to launch balls with varying speed, spin, direction, delay, etc. according to the selected Lesson Plan.

Similar to multi-user embodiments, a player with a coaching device 100 establishes a communication session with ball machine 116 using a conventional "handshake" or other suitable discovery/connection mechanism. The player may also use her coaching device 100 to configure ball machine 116 and/or control other aspects of ball machine 116.

In an embodiment, Tennis Events derived by coaching device 100 may also or alternatively be communicated to an observer, for example a coach with a tablet, computer, or mobile device running an application and communicating with coaching device 100 via transceiver 210. As with multi-user and ball machine embodiments, Tennis Events are communicated via messages and may be accompanied by other information such as metrics. Such an embodiment enables an observer to review metrics and other information about the player in real-time. In the same or an alternative embodiment, a coaching device 100 may receive real-time Notifications and/or Calculations from the observer. For example, the observer may select one or more Notifications using the application on his or her device for transmission to coaching device 100, which may then execute the Notifications immediately or at a time determined by a Lesson Plan.

In the same or an alternative embodiment, the observer may speak into a microphone on his or her device, and the observer's voice will be transmitted to coaching device 100 for immediate announcement or at a time determined by a Lesson Plan. Such an embodiment, for example, permits a coach to instruct a player from a distance without having to shout and potentially disturb others. Similarly, in an embodiment, the player may speak into a microphone included in or connected to interface 202 in coaching device 100, and the player's voice may be transmitted via transceiver 210 to the observer and/or another player. For example, coaching device 100 may be configured to record and transmit a player's voice in response to the player pressing a button on coaching device 100 or speaking a voice command. In this manner, coaching device 100 may act as a two-way radio, thereby permitting players to communicate with other players and coaches without having to shout.

In an embodiment, players may also speak voice commands to interact with ball machine 116. In such an embodiment, interface 202 receives the voice commands and transmits them via transceiver 210 to the coaching device 100 connected to the ball machine 116. The coaching device 100 at the ball machine 116 may then instruct the ball machine accordingly. For example, a player may command the ball machine 116 to launch a shot or a particular type of shot, or to stop launching shots altogether in accordance with a selected Lesson Plan.

In an embodiment, Tennis Events may be communicated to other types of devices. For example, coaching device 100 may communicate a Tennis Event message to a camera that is programmed to take pictures or video of the player upon the occurrence of certain Tennis Events.

The majority of the foregoing description is directed to a tennis embodiment, but other embodiments are also contemplated. For example, the invention could be used in other paddle/racket sports (e.g., table tennis, racketball, badminton, etc.). The invention could also be used when practicing or playing sports involving a club or stick (e.g., golf, baseball, cricket), whereby the coaching device 100 is secured to or integrated within some portion of the club or stick, or worn on the body of the player, and provides feedback to the player. Such other embodiments operate in the same fashion as the tennis embodiment, except that events are logically tied to aspects of the corresponding sport.

The present invention can be realized in hardware or a combination of hardware and software. The invention can be realized in a centralized fashion in one system, or in a distributed fashion where different elements are spread across several interconnected systems. Any kind of computer system or other apparatus adapted for carrying out the methods described herein is suitable. A typical combination of hardware and software can be a general-purpose computer system with a computer program that, when being loaded and executed, controls the system such that it carries out the methods described herein.

The present invention, as already noted, can be embedded in a computer program product, such as a computer-readable storage medium or device which when loaded in a computer system is able to carry out the different methods described herein. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

The foregoing disclosure has been set forth merely to illustrate the invention and is not intended to be limiting. It will be appreciated that modifications, variations and additional embodiments are covered by the above teachings and within the purview of the appended claims without departing from the spirit and intended scope of the invention. Other logic may also be provided as part of the exemplary embodiments but are left out here so as not to obfuscate the present invention. Since modifications of the disclosed embodiments incorporating the spirit and substance of the invention may occur to persons skilled in the art, the invention should be construed to include everything within the scope of the appended claims and equivalents thereof.

The invention claimed is:

1. A system, comprising:
    a first wearable coaching device worn on a first tennis player's wrist;
    a second wearable coaching device worn on a second tennis player's wrist;
    wherein each of the first and second wearable coaching devices comprise:
        at least one sensor;
        at least one wireless transceiver;
        at least one interface;
        at least one processor; and
        at least one memory; and
    wherein each of the first and second wearable coaching devices are configured to:
        detect, using the at least one sensor, a local impact of a tennis ball striking a tennis racket;
        transmit, using the at least one wireless transceiver, a message indicative of the local impact to the other coaching device of the first and second wearable coaching devices;
        receive, using the at least one wireless transceiver, the message from the other coaching device of the first and second wearable coaching devices;
        receive, using the at least one interface, player input to select a lesson plan from among a plurality of lesson plans stored in the at least one memory, wherein each of the plurality of lesson plans is associated with a plurality of recorded voice messages, and wherein each of the plurality of recorded voice messages instructs at least one of the first tennis player and the second tennis player to perform a tennis action;
        in response to at least one of detecting the local impact and receiving the message, determine, using the at least one processor, a recorded voice message from the plurality of recorded voice messages based on the selected lesson plan; and
        output, using the at least one interface, the determined recorded voice message.

2. The system of claim 1, wherein the at least one processor determines the recorded voice message from the plurality of recorded voice messages according to a random order.

3. The system of claim 1, wherein the at least one processor determines the recorded voice message from the plurality of recorded voice messages according to a fixed order, and wherein the order is defined by the selected lesson plan.

4. The system of claim 1, wherein the at least one processor determines the recorded voice message from the plurality of recorded voice messages based on whether the local impact occurred at the first or second coaching device.

5. The system of claim 1, wherein one or more of the plurality of recorded voice messages was recorded by the first tennis player or the second tennis player.

6. The system of claim 1, wherein each of the plurality of lesson plans is associated with its own unique set of recorded voice messages.

7. A wearable coaching device that is worn on a tennis player's wrist and provides real-time coaching instructions to the tennis player, comprising:
    at least one sensor;
    at least one wireless transceiver;
    at least one interface;
    at least one processor; and
    at least one memory;
    wherein the wearable coaching device is configured to:
        detect, using the at least one sensor, a local impact of a tennis ball striking a tennis racket;
        transmit, using the at least one wireless transceiver, a first message indicative of the local impact to at least one other wearable coaching device;
        receive, using the at least one wireless transceiver, a second message from the at least one other wearable coaching device;
        receive, using the at least one interface, player input to select a lesson plan from among a plurality of lesson plans stored in the at least one memory, wherein each of the plurality of lesson plans is associated with a plurality of recorded voice messages, and wherein each of the plurality of recorded voice messages instructs the tennis player to perform a tennis action;

in response to at least one of detecting the local impact and receiving the second message, determine, using the at least one processor, a recorded voice message from the plurality of recorded voice messages based on the selected lesson plan; and output, using the at least one interface, the determined recorded voice message.

8. The wearable coaching device of claim 7, wherein the at least one processor determines the recorded voice message from the plurality of recorded voice messages according to a random order.

9. The wearable coaching device of claim 7, wherein the at least one processor determines the recorded voice message from the plurality of recorded voice messages according to a fixed order, and wherein the order is defined by the selected lesson plan.

10. The wearable coaching device of claim 7, wherein the at least one processor determines the recorded voice message from the plurality of recorded voice messages based on the local impact or the received second message.

11. The wearable coaching device of claim 7, wherein one or more of the plurality of recorded voice messages was recorded by the tennis player.

12. The wearable coaching device of claim 7, wherein each of the plurality of lesson plans is associated with its own unique set of recorded voice messages.

13. A method implemented on a wearable coaching device for providing real-time coaching instructions to a tennis player, comprising:

detecting, by a first wearable coaching device, a local impact of a tennis ball striking a tennis racket;

wirelessly transmitting a first message indicative of the local impact from the first wearable coaching device to a second wearable coaching device;

receiving, by the first wearable coaching device, a second message from the second wearable coaching device;

receiving, by the first wearable coaching device, player input to select a lesson plan from among a plurality of lesson plans stored in the first wearable coaching device, wherein each of the plurality of lesson plans is associated with a plurality of recorded voice messages, and wherein each of the plurality of recorded voice messages instructs the tennis player to perform a tennis action;

in response to at least one of detecting the local impact and receiving the second message, determining, by the first wearable coaching device, a recorded voice message from the plurality of recorded voice messages based on the selected lesson plan; and outputting, by the first wearable coaching device, the determined recorded voice message.

14. The method of claim 13, further comprising determining, by at least one processor, the recorded voice message from the plurality of recorded voice messages according to a random order.

15. The method of claim 13, further comprising determining, by at least one processor, the recorded voice message from the plurality of recorded voice messages according to a fixed order, and wherein the order is defined by the selected lesson plan.

16. The method of claim 13, further comprising determining, by at least one processor, the recorded voice message from the plurality of recorded voice messages based on the local impact or the received second message.

17. The method of claim 13, wherein one or more of the plurality of recorded voice messages was recorded by the tennis player.

18. The method of claim 13, wherein each of the plurality of lesson plans is associated with its own unique set of recorded voice messages.

* * * * *